United States Patent
Pallapa et al.

(10) Patent No.: US 10,455,397 B1
(45) Date of Patent: Oct. 22, 2019

(54) CONTEXT AWARE SUBSCRIBER SERVICE

(71) Applicant: West Corporation, Omaha, NE (US)

(72) Inventors: Gautham Pallapa, Omaha, NE (US); Santhosh Shetty, Omaha, NE (US)

(73) Assignee: West Corporation, Omaha, NE (US)

( * ) Notice: Subject to any disclaimer, the term of this patent is extended or adjusted under 35 U.S.C. 154(b) by 0 days.

(21) Appl. No.: 15/940,214

(22) Filed: Mar. 29, 2018

(51) Int. Cl.
| | |
|---|---|
| *H04W 4/90* | (2018.01) |
| *A61B 5/00* | (2006.01) |
| *H04W 4/02* | (2018.01) |
| *A61B 5/021* | (2006.01) |
| *A61B 5/08* | (2006.01) |
| *A61B 5/0476* | (2006.01) |
| *A61B 5/024* | (2006.01) |

(52) U.S. Cl.
CPC ............ *H04W 4/90* (2018.02); *A61B 5/747* (2013.01); *A61B 5/021* (2013.01); *A61B 5/024* (2013.01); *A61B 5/0476* (2013.01); *A61B 5/0816* (2013.01); *A61B 5/4803* (2013.01); *H04W 4/02* (2013.01)

(58) Field of Classification Search
CPC ......... H04W 4/50; H04W 4/90; H04W 64/00; H04W 76/30; H04W 4/23
USPC ............................ 340/479; 455/404.1, 404.2
See application file for complete search history.

(56) References Cited

U.S. PATENT DOCUMENTS

| | | | | |
|---|---|---|---|---|
| 6,416,471 B1* | 7/2002 | Kumar | ................ | G06F 19/3418 600/300 |
| 6,477,575 B1* | 11/2002 | Koeppel | ................ | G06Q 30/02 709/224 |
| 8,208,891 B2* | 6/2012 | Jacobs | ............... | H04B 7/15507 455/404.1 |
| 8,942,661 B2* | 1/2015 | Stahlin | ................ | H04L 12/6418 340/479 |
| 8,955,001 B2* | 2/2015 | Bhatia | .................. | H04N 21/252 725/12 |
| 9,148,513 B2* | 9/2015 | Tadayon | ................. | H04W 4/50 |
| 9,160,859 B2* | 10/2015 | Tadayon | ................. | H04W 4/50 |
| 9,161,194 B2* | 10/2015 | Hasegawa | ............... | H04W 4/90 |
| 9,172,811 B2* | 10/2015 | Tadayon | ................. | H04W 4/50 |
| 9,239,743 B2* | 1/2016 | Gupta | ................. | G06F 11/0766 |
| 9,325,850 B2* | 4/2016 | Tadayon | ................. | H04W 4/50 |
| 9,332,125 B2* | 5/2016 | Tadayon | ................. | H04W 4/50 |
| 9,338,300 B2* | 5/2016 | Tadayon | ................. | H04W 4/50 |
| 9,438,737 B2* | 9/2016 | Tadayon | ................. | H04W 4/50 |
| 9,440,749 B1* | 9/2016 | Ye | ........................... | B64D 3/00 |
| 9,452,844 B1* | 9/2016 | Ye | ........................... | B64D 3/00 |
| 9,497,324 B2* | 11/2016 | Tadayon | ................. | H04W 4/50 |
| 9,692,902 B2* | 6/2017 | Tadayon | ................. | H04W 4/50 |
| 9,771,160 B2* | 9/2017 | Ye | ........................... | B64D 3/00 |
| 9,838,343 B2* | 12/2017 | Kallio | .................... | H04L 51/066 |
| 9,906,930 B2* | 2/2018 | Blando | ................... | H04W 4/90 |
| 9,996,990 B2* | 6/2018 | Slusar | ................... | G07C 5/0808 |
| 9,998,856 B2* | 6/2018 | Edge | .................. | H04W 64/00 |
| 10,003,945 B2* | 6/2018 | Papakonstantinou | ....................... | H04W 4/023 |
| 10,033,819 B2* | 7/2018 | Thanayankizil | ...... | H04W 76/30 |

(Continued)

*Primary Examiner* — William D Cumming

(57) ABSTRACT

One example method of operation provides receiving, at a server, event data generated by a user device indicating an emergency event, initiating an emergency application on the user device, processing the event data to identify whether the event data exceeds an emergency status threshold, transmitting a notification to the user device, and based on a response from the user device, notifying third party services of the emergency event.

21 Claims, 6 Drawing Sheets

(56) References Cited

U.S. PATENT DOCUMENTS

| | | | | |
|---|---|---|---|---|
| 10,034,034 B2* | 7/2018 | Bhatia | .................. | H04N 21/252 |
| 2006/0265418 A1* | 11/2006 | Dolezal | .................. | G06Q 10/10 |
| 2010/0279647 A1* | 11/2010 | Jacobs | ............... | H04B 7/15507 |
| | | | | 455/404.1 |
| 2012/0157795 A1* | 6/2012 | Chiu | .................. | G06F 19/3418 |
| | | | | 600/301 |
| 2012/0252398 A1* | 10/2012 | Jacobs | ............... | H04B 7/15507 |
| | | | | 455/404.1 |
| 2013/0100268 A1* | 4/2013 | Mihailidis | ............... | G08B 21/02 |
| | | | | 348/77 |
| 2014/0109111 A1* | 4/2014 | Gupta | ................ | G06F 11/0766 |
| | | | | 719/318 |
| 2014/0143304 A1* | 5/2014 | Hegarty | .............. | G06F 11/3438 |
| | | | | 709/203 |
| 2015/0324539 A1* | 11/2015 | Chiu | .................. | G06F 19/3418 |
| | | | | 705/2 |
| 2015/0356853 A1* | 12/2015 | Cronin | ................ | G08B 21/182 |
| | | | | 340/669 |
| 2016/0100302 A1* | 4/2016 | Barash | .................. | H04W 4/90 |
| | | | | 455/404.2 |
| 2016/0142894 A1* | 5/2016 | Papakonstantinou | ........................ | H04W 4/023 |
| | | | | 455/404.1 |
| 2016/0257415 A1* | 9/2016 | Ye | ............................ | B64D 3/00 |
| 2016/0257421 A1* | 9/2016 | Ye | ............................ | B64D 3/00 |
| 2016/0302050 A1* | 10/2016 | Blando | .................. | H04W 4/90 |
| 2017/0029128 A1* | 2/2017 | Ye | ............................ | B64D 3/00 |
| 2017/0092109 A1* | 3/2017 | Trundle | .............. | G08B 25/006 |
| 2018/0012471 A1* | 1/2018 | Bauer | ................ | G08B 21/0269 |
| 2018/0114378 A1* | 4/2018 | Slusar | .................. | G07C 5/0808 |
| 2018/0199179 A1* | 7/2018 | Rauner | .................. | H04W 4/90 |

* cited by examiner

US 10,455,397 B1

CONTEXT AWARE SUBSCRIBER SERVICE

TECHNICAL FIELD OF THE APPLICATION

This application relates to providing mobile services to a subscriber, and more particularly, to tracking a user's location and integrating a subscriber status with a mobile device functionality to optimize emergency monitoring and support services.

BACKGROUND OF THE APPLICATION

Conventionally, when a customer subscribes to a home alarm service or other related emergency service providers, such as ONSTAR for remote vehicle emergency services, the subscriber is only subscribing to a particular location, such as their one or two identified vehicles, or, a particular house in which they reside on a daily basis. However, as the services become more advanced and less hardware dependent, meaning the need for sensors, wires, electronic wiring, etc., is reduced, the more mobile and adaptable the services become. For example, ONSTAR tracks vehicle emergency conditions which could just as easily be sensed by a user's mobile device and which does not require extensive sensors hardwired to a particular vehicle. As a result, if a subscriber is renting a car for a vacation, they may be able to receive GPS tracking and safety support based on information identified from just their mobile device or other nearby communication devices.

SUMMARY OF THE APPLICATION

Example embodiments of the present application provide a method that includes at least one of receiving, at a server, event data generated by a user device indicating an emergency event, initiating an emergency application on the user device, processing the event data to identify whether the event data exceeds an emergency status threshold, transmitting a notification to the user device, and based on a response from the user device, notifying third party services of the emergency event.

Another example embodiment of the present application may include an apparatus that includes a receiver configured to receive event data generated by a user device indicating an emergency event and a processor configured to initiate an emergency application, process the event data to identify whether the event data exceeds an emergency status threshold and a transmitter configured to transmit a notification to a user device, and based on a response from the user device, the transmitter notifies third party services of the emergency event.

Example embodiments of the present application provide a non-transitory computer readable storage medium configured to store instructions that when executed cause a processor to perform at least one of receiving, at a server, event data generated by a user device indicating an emergency event, initiating an emergency application on the user device, processing the event data to identify whether the event data exceeds an emergency status threshold, transmitting a notification to the user device, and based on a response from the user device, notifying third party services of the emergency event.

DETAILED DESCRIPTION OF THE APPLICATION

Figure 1:
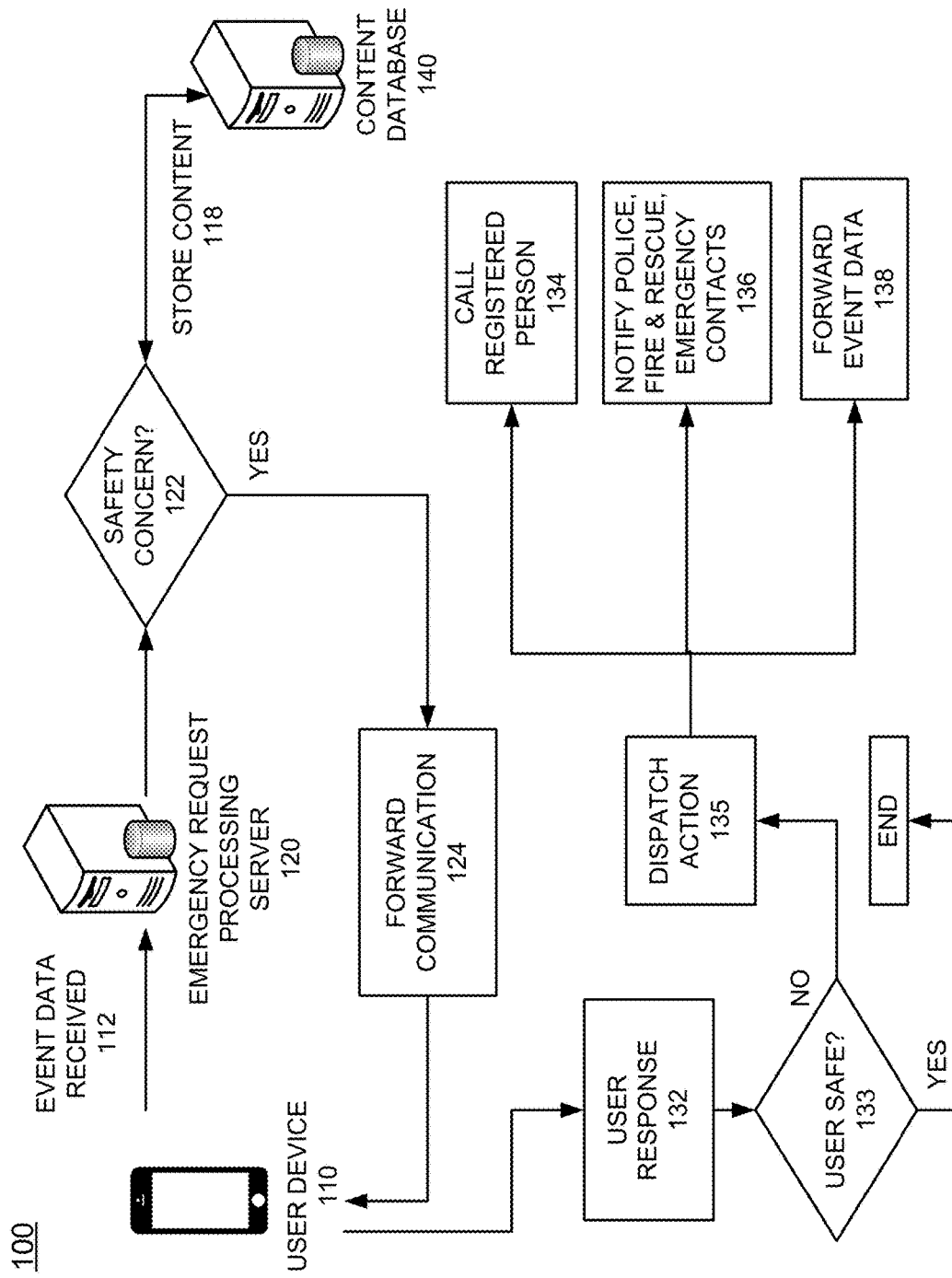
FIG. 1 illustrates an example communication logic diagram for receiving and processing emergency event data according to example embodiments of the present application.

It will be readily understood that the components of the present application, as generally described and illustrated in the figures herein, may be arranged and designed in a wide variety of different configurations. Thus, the following detailed description of the embodiments of a method, apparatus, and system, as represented in the attached figures, is not intended to limit the scope of the application as claimed, but is merely representative of selected embodiments of the application.

The features, structures, or characteristics of the application described throughout this specification may be combined in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment of the present application. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments.

In addition, while the term "message" has been used in the description of embodiments of the present application, the application may be applied to many types of network data, such as, packet, frame, datagram, etc. For purposes of this application, the term "message" also includes packet, frame, datagram, and any equivalents thereof. Furthermore, while certain types of messages and signaling are depicted in exemplary embodiments of the application, the application is not limited to a certain type of message, and the application is not limited to a certain type of signaling.

An application which may be operated on the mobile device may provide a context aware subscriber assistance system that offers a response system to context related triggers. For example, the mobile device may provide global positioning satellite (GPS) data, accelerometer data, etc., which may be tracked by a third party service provider to which the user device is subscribed. The GPS and the accelerometer features may be identified as active contexts which provide contextual information.

In operation, a user traveling in a transport vehicle may experience a sudden deceleration and a combination of context triggers may be identified and evaluated to determine the possibility of a vehicle crash. For example, a GPS context may demonstrate that a phone traveling in the transport is no longer moving and GPS coordinates have stopped accumulating or are no longer indicating displacement over time. In this event, the monitoring service may preliminarily identify the event as a car crash and may initiate certain actions. For instance, the user device may be sent a text message, an email or called to determine whether the event is problematic to the safety of the user. Other contexts which may be used to identify threats to the subscriber which may include biometric measurements, such as pulse, heart rate, breathing rate, blood pressure, etc., which may indicate that the user is hurt or safe.

In another example, children may be at risk for kidnapping or being subjected to circumstances or locations which are uncommon or foreign given their regular routines. The child may have their own smartphone or smartwatch or other smart device carried by the child. In the event that the child's movements are off-course from a known course of movement, an alarm may trigger to notify all interested parties to immediately come to the child's aid. For example, if the child is known to be in a certain area after school each day and the child is now traveling in a car down a road unrecognized by the monitoring service, an alarm may be triggered to identify the present location of the child and notify interested parties. Also, if the device is removed from the child and discarded, the child's movement will then no longer correspond to that of the child's anticipated movements, such as to and from school with respect to a home location.

FIG. 1 illustrates an example communication logic diagram for receiving and processing emergency event data according to example embodiments of the present application. Referring to FIG. 1, the configuration 100 includes a user device 110 which is carried with a user and which is associated with a user profile that is registered for the emergency service monitoring provided by a third party service provider. In this example, the emergency request processing server 120 is responsible for monitoring actions and events on the user device 110. The user device may have an application which pre-processes data which is identified as potentially life-threatening, such event data 112 may be identified on the user device 110 prior to being identified by the server 120.

In another example operation, a sudden deceleration of the user device 110 being located inside of a moving vehicle may be identified as a potential danger event on the user device 110. As a result, the server 120 may either periodically poll the user device for potential events, or the device may periodically send a heartbeat signal or other event signals to the server, in this case, the information, which may include location, accelerometer data, etc., is logged in memory and the data associated with the event (i.e., GPS data, accelerometer data, etc.), may then be sent with an event pre-process notification indicating a potential emergency event to the server 120 for additional processing and actions. If the server 120 compares the event data to known emergency event data information (i.e., threshold data) and an emergency threshold is exceeded or any other emergency trigger is identified, then the safety concern 122 may be deemed a credible concern and the server 120 may then attempt to contact the user device 110, by forwarding a communication 124 to the user device 110, such as "are you ok?". The user can then decide whether to respond with a message, such as "I'm fine", or "I need help", see FIG. 2.

All the content shared, such as GPS data, accelerometer data, as measured by the user device, images, videos, audio, biometrics (e.g., vital signs), etc., may be sent as content 118 which is stored in a content database 140 for future reference. Once the user responds 132 and the user is identified as being safe 133, the process ends. If however, the user is identified as being hurt or unresponsive, an action may be created 135 to dispatch to any first responders 136, notify registered persons 134 and/or forward the event data 138 to other interested parties tracking the user condition status.

Figure 2:
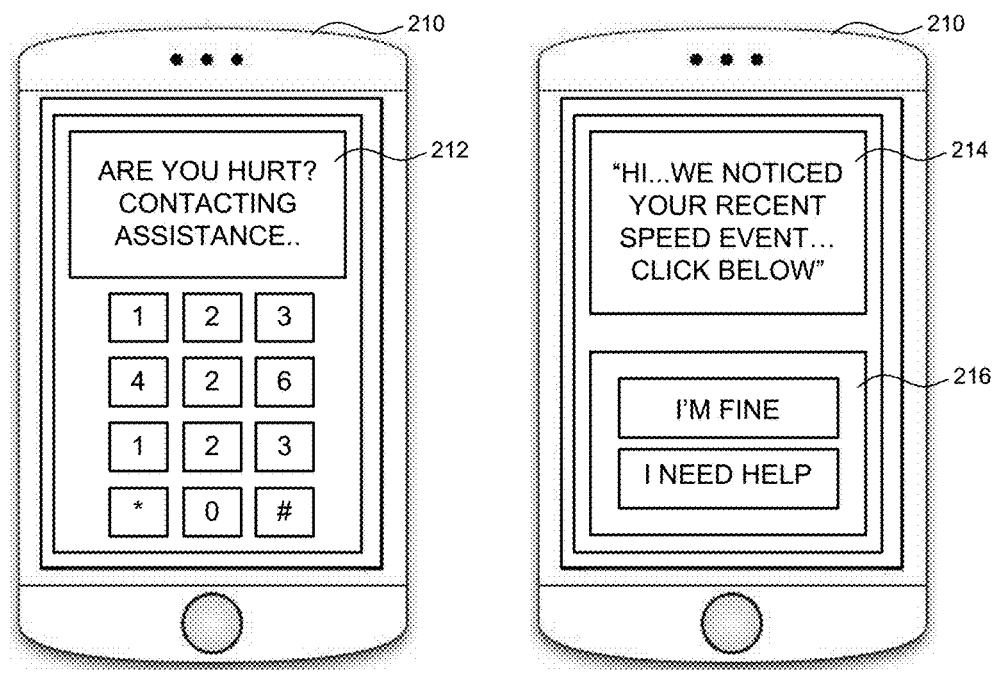
FIG. 2 illustrates a user device user interface populated with emergency session management information according to example embodiments of the present application.

FIG. 2 illustrates a user device user interface populated with emergency session management information according to example embodiments of the present application. Referring to FIG. 2, the example 200 includes a user device 210 may have an application that corresponds to the emergency actions, or the user may just receive an email or text message outside of an application. The event data which is sent to the server may trigger a message, such as a notification to confirm the user health status "are you hurt?" 212 or some type of question soliciting a response. The user may see the messages 214 and respond with automated virtual buttons 216 to either cancel the alert or provoke and elevate the concern to an actionable event 216 to notify the authorities.

Figure 3:
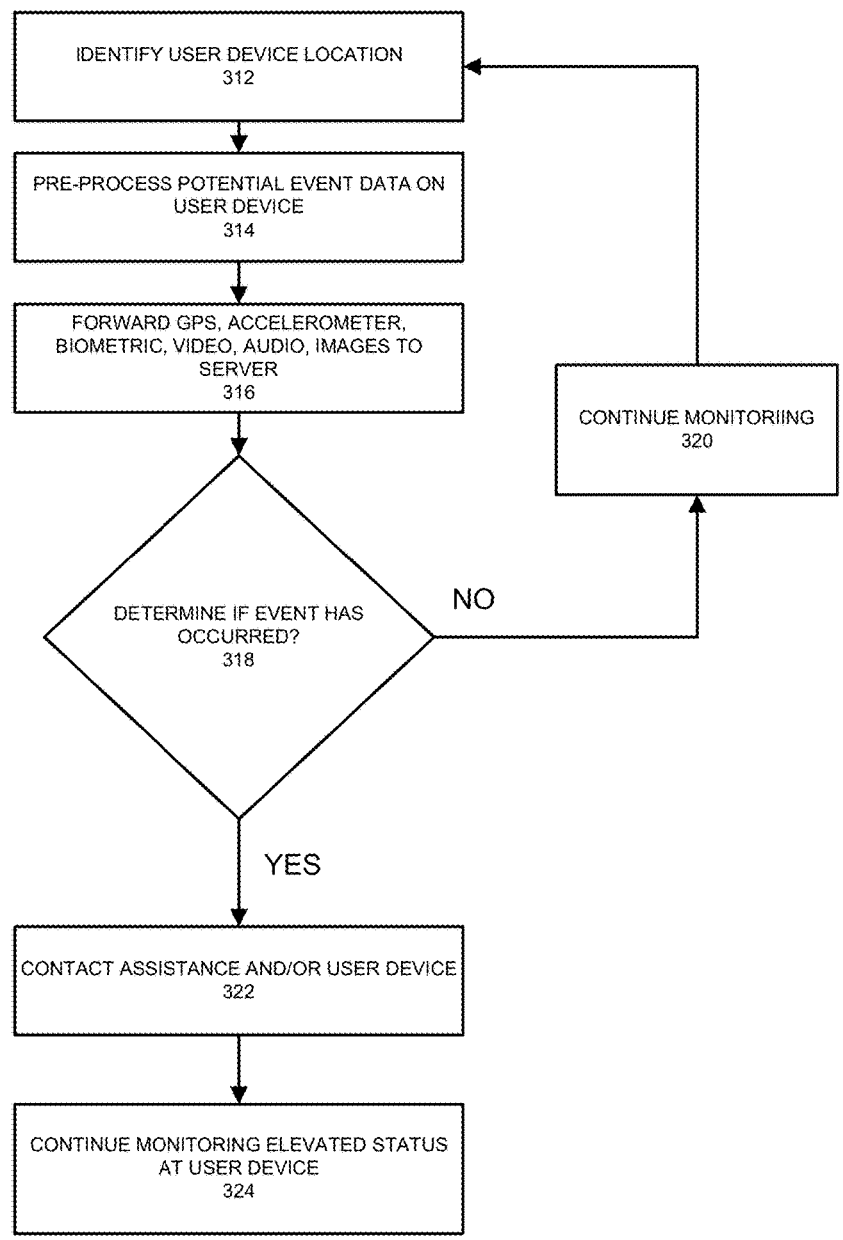
FIG. 3 illustrates a flow diagram for managing emergency event management sessions according to example embodiments of the present application.

FIG. 3 illustrates a flow diagram for managing emergency event management sessions according to example embodiments of the present application. Referring to FIG. 3, the flow diagram 300 demonstrates an example where the event data is processed to determine a course of action. For example, the application may monitor a user device's location 312 as part of an ongoing monitoring function to track and ensure the safety of the user via the user device. When an event occurs, which has the potential to be a true emergency event, the initial screening procedure may include a pre-process instance at the user device 314. This pre-processing may include an initial determination as to whether the user has experienced a traumatic event worth notifying the emergency server or not. Also, the potential event may be logged in the user device until the server is able to retrieve the event so a full processing procedure can be performed to identify the event in greater detail and perform the necessary actions.

Continuing with the same example, the various metrics obtained by the user device (e.g., biometric data, GPS data, accelerometer data, video data, audio data, images, etc.) may be forwarded 316 to the server for comparison to baseline events stored in memory to determine whether an event 318 has occurred. This additional processing may determine whether the event is severe and requires immediate action. The processing may be performed and if no emergency event is identified then the process may revert to ongoing monitoring 320 for future potential events. If the event is deemed an emergency, then assistance may be contacted on behalf of the user 322, also the user device may be contacted to confirm the event. However, many times a user will not respond, and thus the result will be an emergency designation. The user device may be continuously monitored 324 for any changes in the elevated status. Once the situation is deemed an emergency, the user device may be requested to automatically provide content for ongoing analysis, such as video, audio, images, etc.

Figure 4:
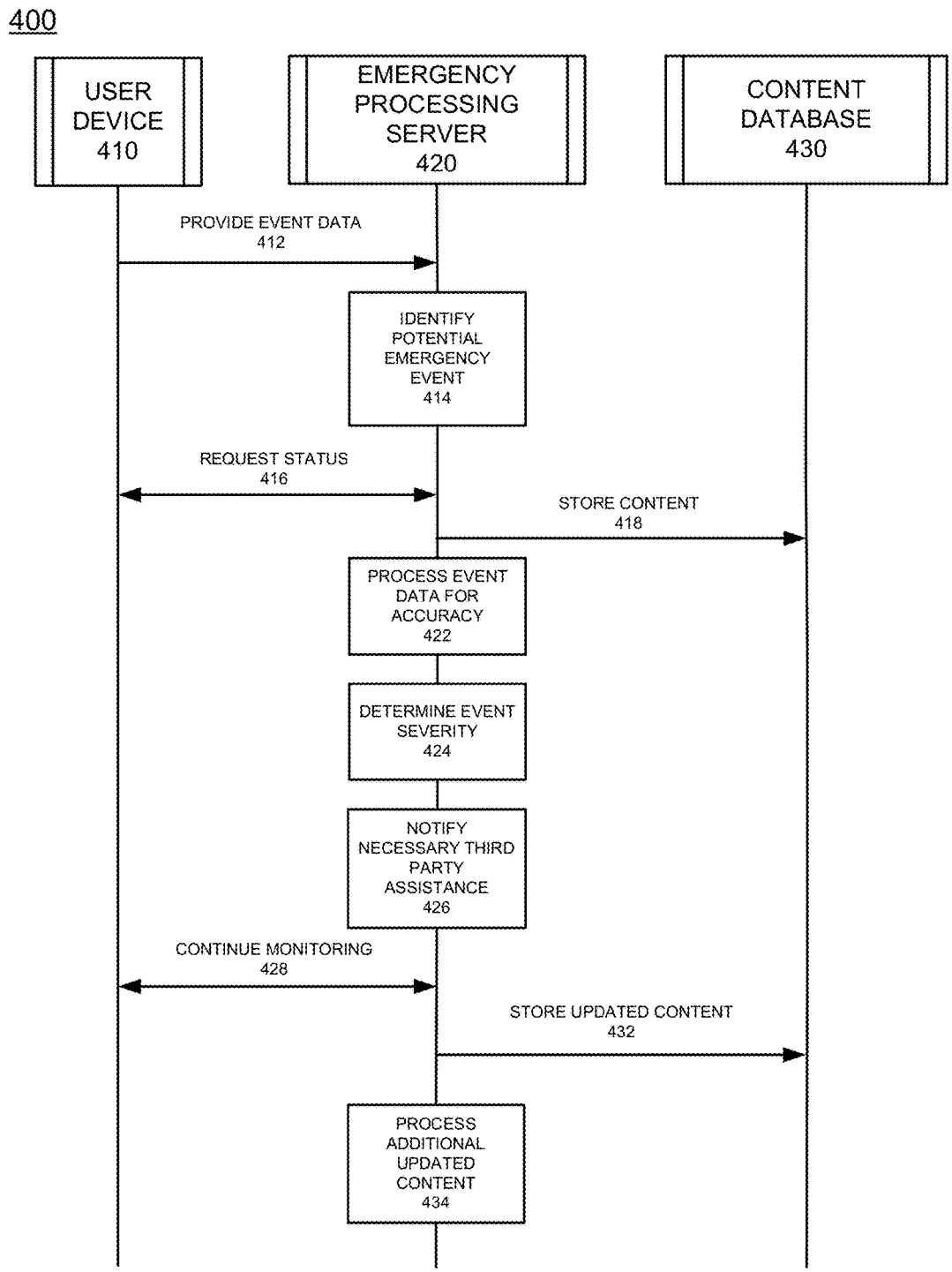
FIG. 4 illustrates a system signaling diagram for processing an emergency event configuration according to example embodiments of the present application.

FIG. 4 illustrates a system signaling diagram 400 for processing an emergency event configuration according to example embodiments of the present application. Referring to FIG. 4, the user device 410 may communicate with the emergency server 420 to share recent event data pertaining to a recent data capture of an elevated status or situation. One example method of operation may include receiving, at the server 420, event data 412 generated by the user device 410 indicating an emergency event. The process may also include initiating an emergency application on the user device 410. The server may preliminarily designate the event an emergency event 414 based on a pre-processing operation conducted by the user device when the event data triggers an analysis. For example, a threshold change in GPS coordinate changes since a previous GPS location update may indicate a deceleration associated with a motor vehicle accident. An initial analysis may dictate an immediate need for assistance. However, the user device may have been dropped from someone's pocket riding a bike in a very fast manner, and if the server contacts the user and identifies that no emergency exists, the event may be cancelled, especially after a user response message indicating that there is no problem.

The server may request a status 416 from the user device after any identified event or potential emergency. The user device will either respond with a confirmation of the emergency, a confirmation of no emergency or no response. The content received may include the GPS data, accelerometer data, biometric/vital sign information, video, audio, still images, triangulation position information from nearby cell towers, etc. Any of the content 418 may be stored for future reference and for additional analysis. The event data may be processed 422 for accuracy and to identify whether a true event has occurred, the magnitude of the event and/or the likelihood that certain emergency services are required. The processing may also include processing the event data received to identify whether the event data exceeds an emergency status threshold for any of the content data categories, the severity of the event 424 must be identified to provide adequate response services. Based on a response from the user device certain third party services 426 may be notified of the emergency event.

In the time after the initial event was identified, monitoring may be continued 428 to ensure the user is still safe especially after some type of emergency has been identified. The user device 410 may automatically be configured through the emergency application to offer images, video, audio, questions requiring answers in text message format, voice samples, etc. Such data may be used to determine the continued condition and safety of the user. All such content may also be forwarded and updated 432 to a content database 430. The additionally received updated content may be processed 434 to identify such emergency instances and whether a change in the initial course of action should be performed.

The event data may include accelerometer data, global positioning satellite data, biometric data, etc., and any other type of data which could provide assistance with identifying a potential tragic event. The biometric data may include one or more of a user heart rate, blood pressure, breathing rate, brain activity, and a voice sample. The procedure may also include determining an event severity based on the event data being compared to pre-stored model event data based on emergency events, retrieving a user record associated with the user device, and identifying user attributes. The procedure may also include monitoring a user status of the user based on updates received from the user device, and determining whether to elevate an emergency event status based on the user status. The method may also include determining the user status based on event data received from the updates received form the user device.

Figure 5:
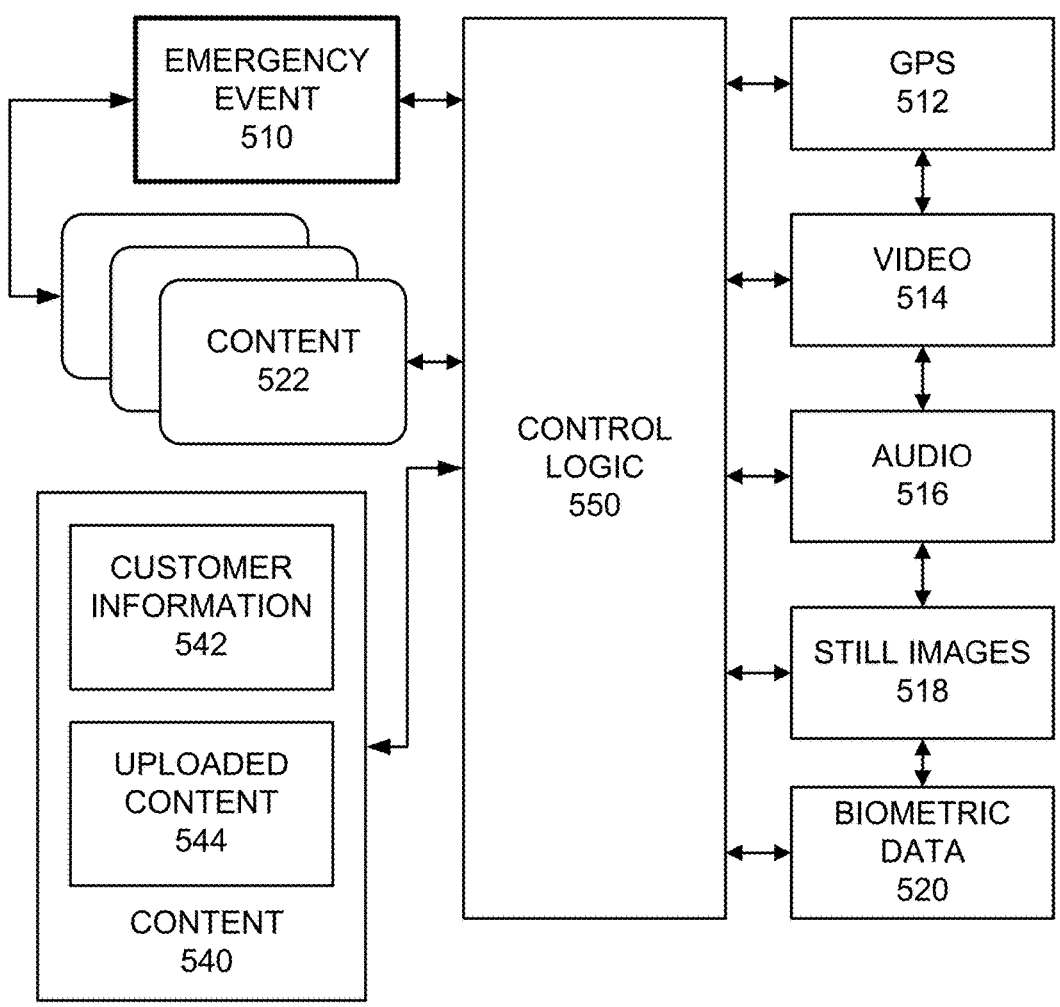
FIG. 5 illustrates a logic processing diagram with input data, a processing module and output data according to example embodiments of the present application.

FIG. 5 illustrates a logic processing diagram with input data, a processing module and output data according to example embodiments of the present application. Referring to FIG. 5, the logic processor 550 may have various input data and output data that is received, retrieved and processed to achieve results which are favorable to the objectives of the example embodiments. For instance, the emergency events 510 are received and processed along with content 522 captured from a user device. The content 540 may include various uploaded content 544 that is received and may also include customer information 542 identifying the user device registered owner. The data information may include GPS data 512, video 514, audio 516, still images 518 and biometric data 520 received the user device.

The operations of a method or algorithm described in connection with the embodiments disclosed herein may be embodied directly in hardware, in a computer program executed by a processor, or in a combination of the two. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components. For example, FIG. 6 illustrates an example network element 600, which may represent any of the above-described network components of the other figures.

Figure 6:
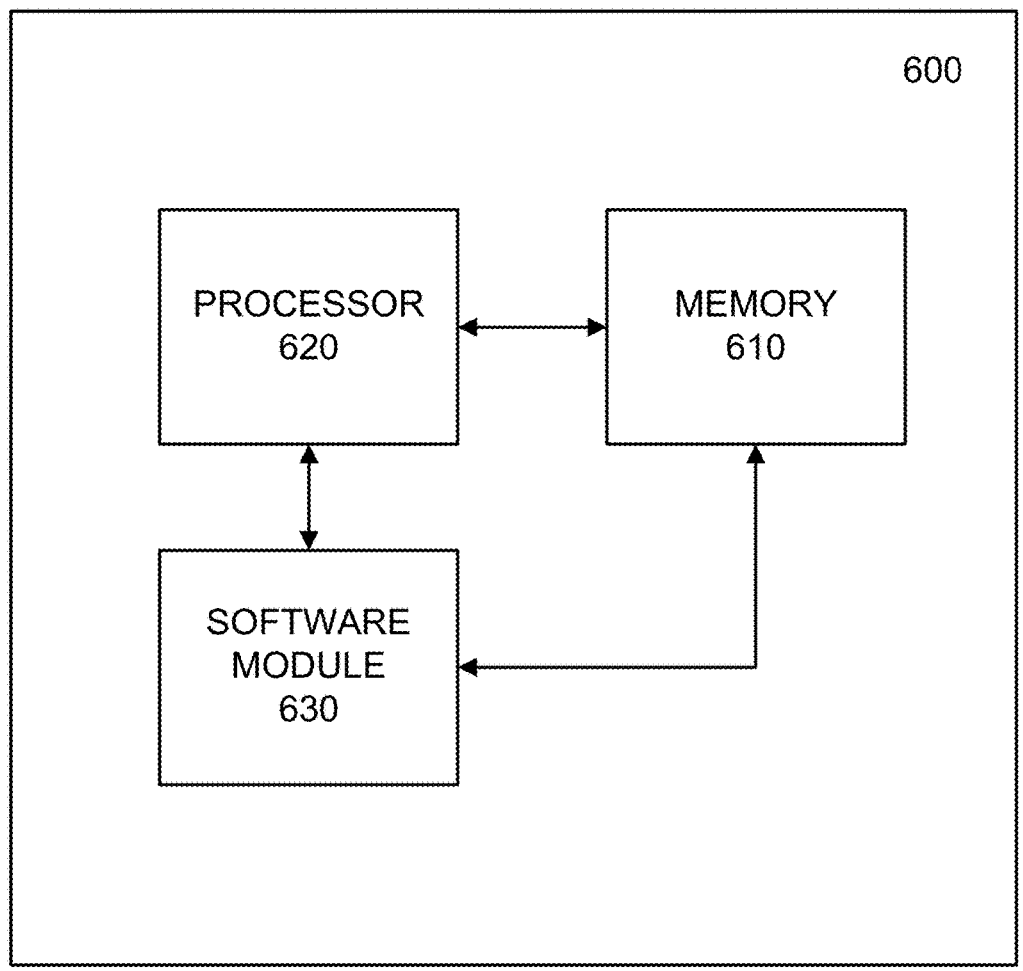
FIG. 6 illustrates an example network entity device configured to store instructions, software, and corresponding hardware for executing the same, according to example embodiments of the present application.

As illustrated in FIG. 6, a memory 610 and a processor 620 may be discrete components of the network entity 600 that are used to execute an application or set of operations. The application may be coded in software in a computer language understood by the processor 620, and stored in a computer readable medium, such as, the memory 610. The computer readable medium may be a non-transitory computer readable medium that includes tangible hardware components in addition to software stored in memory. Furthermore, a software module 630 may be another discrete entity that is part of the network entity 600, and which contains software instructions that may be executed by the processor 620. In addition to the above noted components of the network entity 600, the network entity 600 may also have a transmitter and receiver pair configured to receive and transmit communication signals (not shown).

Although an exemplary embodiment of the system, method, and computer readable medium of the present application has been illustrated in the accompanied drawings and described in the foregoing detailed description, it will be understood that the application is not limited to the embodiments disclosed, but is capable of numerous rearrangements, modifications, and substitutions without departing from the spirit or scope of the application as set forth and defined by the following claims. For example, the capabilities of the system of the various figures can be performed by one or more of the modules or components described herein or in a distributed architecture and may include a transmitter, receiver or pair of both. For example, all or part of the functionality performed by the individual modules, may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a smartphone or any other suitable computing device, or combination of devices. Presenting the above-described functions as being performed by a "system" is not intended to limit the scope of the present application in any way, but is intended to provide one example of many embodiments of the present application. Indeed, methods, systems and apparatuses disclosed herein may be implemented in localized and distributed forms consistent with computing technology.

It should be noted that some of the system features described in this specification have been presented as modules, in order to more particularly emphasize their implementation independence. For example, a module may be implemented as a hardware circuit comprising custom very large scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module. Further, modules may be stored on a computer-readable medium, which may be, for instance, a hard disk drive, flash device, random access memory (RAM), tape, or any other such medium used to store data.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

It will be readily understood that the components of the application, as generally described and illustrated in the figures herein, may be arranged and designed in a wide variety of different configurations. Thus, the detailed description of the embodiments is not intended to limit the scope of the application as claimed, but is merely representative of selected embodiments of the application.

One having ordinary skill in the art will readily understand that the application as discussed above may be practiced with steps in a different order, and/or with hardware elements in configurations that are different than those which are disclosed. Therefore, although the application has been described based upon these preferred embodiments, it would be apparent to those of skill in the art that certain modifications, variations, and alternative constructions would be apparent, while remaining within the spirit and scope of the application. In order to determine the metes and bounds of the application, therefore, reference should be made to the appended claims.

While preferred embodiments of the present application have been described, it is to be understood that the embodiments described are illustrative only and the scope of the application is to be defined solely by the appended claims when considered with a full range of equivalents and modifications (e.g., protocols, hardware devices, software platforms etc.) thereto.

What is claimed is:

1. A method comprising:
   initiating, via a user device, an emergency application on the user device in response to an event associated with a user of the user device;
   generating, via the user device, event data associated with the event;
   pre-processing, via the user device, the event data to make an initial determination as to whether the event data indicates a potential emergency event based on one or more data thresholds;
   identifying, via the user device, that the event data indicates a potential emergency event;
   transmitting, via the user device, the event data to a remote server for analysis based on the identification of the potential emergency event; and
   receiving, via the user device, a request from the remote server to automatically provide additional data for ongoing analysis by the remote server based on a determination by the remote server that the event data identifies an emergency event.

2. The method of claim 1, wherein the event data comprises one or more of:
   accelerometer data, global positioning satellite data, and biometric data.

3. The method of claim 2, wherein the biometric data comprises one or more of:
   a user heart rate, blood pressure, breathing rate, brain activity, and voice sample.

4. The method of claim 1, wherein the receiving a request from the remote server further comprises:
   receiving, via the user device, a request from the remote server when the analysis by the remote server identifies an emergency event based on the event data being compared to pre-stored model event data based on emergency events.

5. The method of claim 1, further comprising:
   retrieving a user record associated with the user device; and
   identifying user attributes.

6. The method of claim 1, further comprising:
   continuously transmitting, via the user device, information regarding a status of the user based on the request from the remote server.

7. The method of claim 6, further comprising:
   receiving, via the user device, and from the remote server, a request to confirm the existence of an emergency event.

8. A mobile device, comprising:
   a memory to store at least one instruction that when executed by a processor causes the processor to:
   initiate an emergency application in response to an event associated with a user of the mobile device;

generate event data associated with the event;

pre-process the event data to make an initial determination as to whether the event data indicates a potential emergency situation based on one or more data thresholds; and cause a transmitter to transmit the event data to a remote server for analysis, if the initial determination identifies that the event data indicates a potential emergency situation.

9. The mobile device of claim 8, wherein the event data comprises one or more of:

accelerometer data, global positioning satellite data, and biometric data.

10. The mobile device of claim 9, wherein the biometric data comprises one or more of:

a user heart rate, blood pressure, breathing rate, brain activity, and voice sample.

11. The mobile device of claim 8, wherein the memory further is to store at least one instruction that when executed by the processor causes the processor to:

receive a request from the remote server when the analysis by the remote server identifies an emergency event.

12. The mobile device of claim 8, wherein the memory further is to store at least one instruction that when executed by the processor causes the processor to:

retrieve a user record associated with the user device; and identify user attributes.

13. The mobile device of claim 8, wherein the memory further is to store at least one instruction that when executed by the processor causes the processor to:

cause the transmitter to continuously transmit information regarding a status of the user based on the request from the remote server.

14. The mobile device of claim 13, wherein the memory further is to store at least one instruction that when executed by the processor causes the processor to:

receive a request to confirm the existence of an emergency situation from the remote server.

15. A method comprising:

receiving, via a remote server, event data generated by a user device in response to an event associated with a user of the user device, wherein the event data is pre-processed by the user device to make an initial determination as to whether the event data indicates a potential emergency event;

identifying, via the remote server, that the potential emergency event is an emergency event based on an analysis of the event data;

communicating, via the remote server, a request to the user device to automatically provide additional data based on the identification of the emergency event;

performing, via the remote server, an ongoing analysis of the additional data received from the user device; and notifying, via the remote server, a third party service provider of the emergency event.

16. The method of claim 15, wherein the event data comprises one or more of:

accelerometer data, global positioning satellite data, and biometric data.

17. The method of claim 16, wherein the biometric data comprises one or more of:

a user heart rate, blood pressure, breathing rate, brain activity, and voice sample.

18. The method of claim 15, wherein the communicating a request to the user device further comprises:

communicating a request to the user device when the analysis by the remote server identifies an emergency event based on a comparison of the event data to pre-stored model event data based on emergency events.

19. The method of claim 15, further comprising:

retrieving a user record associated with the user device; and identifying user attributes.

20. The method of claim 15, further comprising:

continuously receiving, via the remote server, information regarding a status of the user based on the request from the remote server; and determining, via the remote server, whether to elevate a status associated with the emergency event status based on the status of the user.

21. The method of claim 15, further comprising:

communicating, via the remote server, a request to confirm the existence of the emergency event to the user device; and automatically identifying an existence of the emergency event based on a lack of response to the request.

* * * * *